United States Patent [19]

Naslund

[11] 4,294,582
[45] Oct. 13, 1981

[54] METHOD FOR PROCESSING A BODY LIQUID SPECIMEN

[76] Inventor: Jan I. Naslund, Vassvagen 21, Huddinge, Sweden

[21] Appl. No.: 167,199

[22] Filed: Jul. 9, 1980

Related U.S. Application Data

[63] Continuation-in-part of Ser. No. 62,617, Aug. 1, 1979, abandoned, which is a continuation-in-part of Ser. No. 903,259, May 5, 1978, abandoned.

[30] Foreign Application Priority Data

May 17, 1977 [SE] Sweden .............................. 7705788

[51] Int. Cl.³ ...................... A61B 10/00; G01N 1/10
[52] U.S. Cl. ................. 23/230 B; 128/346; 128/767; 422/102
[58] Field of Search ................. 23/230 B; 422/61, 68, 422/102; 128/346, 767

[56] References Cited

U.S. PATENT DOCUMENTS

| | | | |
|---|---|---|---|
| 3,036,894 | 5/1962 | Forestiere | 422/68 X |
| 3,532,470 | 10/1970 | Rochte | 422/61 |
| 3,579,303 | 5/1971 | Pickering | 422/102 X |
| 3,660,033 | 5/1972 | Schwartz | 128/767 X |
| 3,850,159 | 11/1974 | Langley | 128/767 |
| 3,874,042 | 4/1975 | Eddleman et al. | 128/346 X |
| 3,926,195 | 12/1975 | Bleier et al. | 128/346 |

OTHER PUBLICATIONS

Gradwohl's, "Clinical Laboratory Methods and Diagnosis", The C.V. Mosby Co., Saint Louis, 1970, pp. 924–927 and 1845–1849.

Primary Examiner—Arnold Turk
Attorney, Agent, or Firm—Larson and Taylor

[57] ABSTRACT

A method and device for processing a body liquid specimen used for diagnostical examination. The specimen is brought to settle for a predetermined time in a first chamber of a container which has a second, separate chamber containing a certain amount of a fixative, whereupon a portion of the specimen containing a predetermined amount of a concentrate having high concentration of settled body cells is separated and confined in a third chamber, which is formed by partitioning off a portion of the first chamber. Thereafter the remaining body liquid is removed from the container, and said second and third chambers are interconnected in order to form a common, sealed chamber in which the concentrate is mixed with the fixative.

2 Claims, 13 Drawing Figures

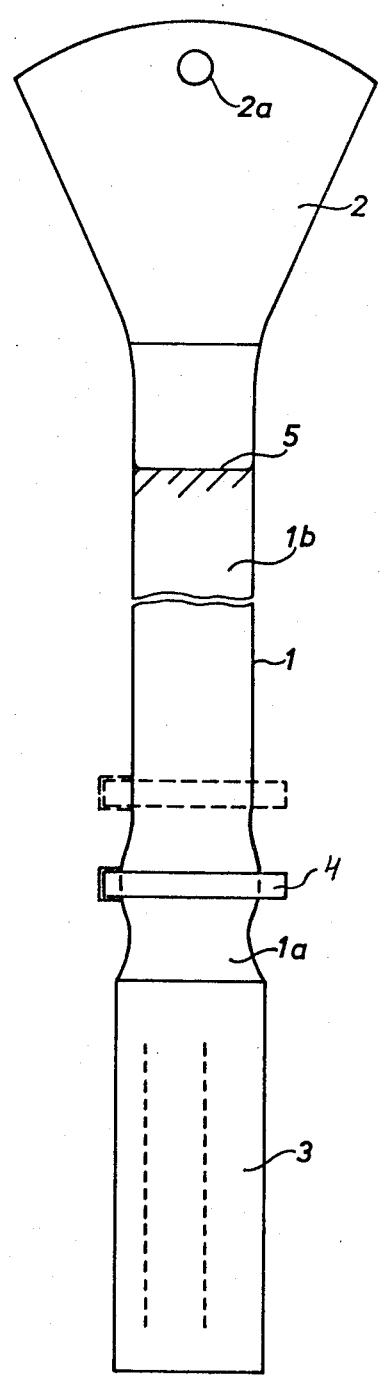
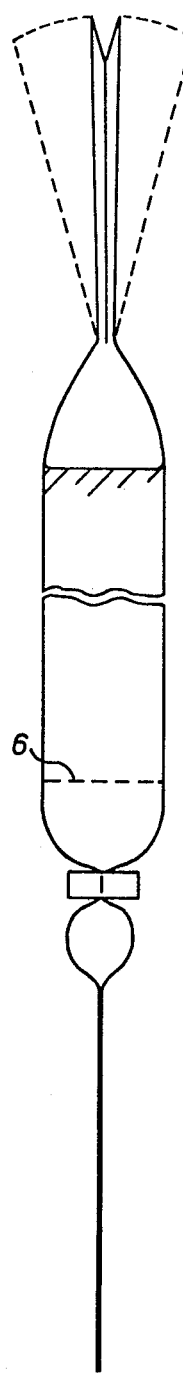
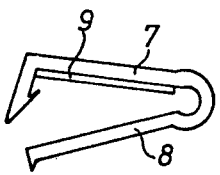
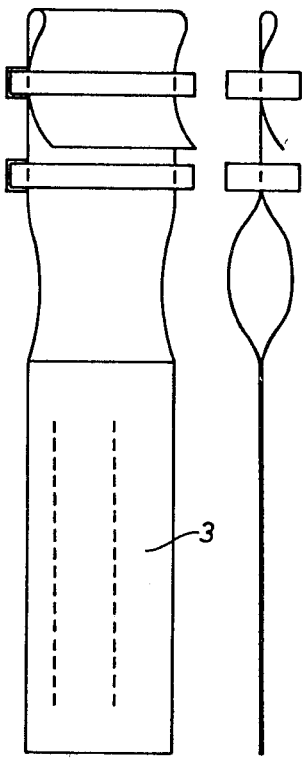
FIG. 1  FIG. 2  FIG. 3  FIG. 4
FIG. 5

METHOD FOR PROCESSING A BODY LIQUID SPECIMEN

CROSS REFERENCES TO RELATED APPLICATIONS

This application is a continuation-in-part of application Ser. No. 062,617 filed Aug. 1, 1979, now abandoned; which in turn is a continuation of application Ser. No. 903,259 filed May 5, 1978, now abandoned.

FIELD OF THE INVENTION

The present invention relates to a method of processing a body liquid specimen intended for diagnostical examination. As examples of body liquids for which the invention is intended to be applied there could be mentioned urine, ascites and pleura liquid.

BACKGROUND OF THE INVENTION

In many diseases it is essential for a successful treatment that the state of the disease can be discovered and a certain diagnosis be made at an early stage. This is the case for instance in tumour diseases, such as cancer, and the prospects of survival of the cancer patient is entirely dependent upon the spreading of the cancer tumour at the point of time when the diagnosis is made.

Diagnosis of tumour diseases can be made by microscopical examination of the appearance and dyeability of body cells, so called cytology, which is made daily in certain hospitals having doctors educated for such examination. Specimens intended for cytological testing can be taken from body tissue by means of pin-pricks or by scraping off a cell specimen from a mucous membrane. The specimen is then processed by a fixative which results in ceasing the metabolism of the cells and their appearance and dyeability being preserved. A small and durable preparation is thereby obtained which is suitable for being forwarded by mail to a laboratory for cytological examination. By this method it has proved possible to discover for instance abdominal cancer at an early stage.

Body cells are continuously rejected from the urinary bladder and the urethra and accompany the urine out. By cytological examination of such cells from a urine specimen it is possible to establish the presence of cancer cells, if any, whereby cancer in the urinary bladder can be diagnosed. Such examination of cells from urine specimens is carried out at present in hospitals in which cytologists are available and in which such examination can consequently be made relatively soon after the specimen has been taken. Cells appearing in urine specimens are destroyed rapidly by putrefaction, whereby a proper microscopical examination thereof is made impossible after only a few hours.

There is a strong desire to be able to collect body liquid specimens, especially urine specimens, for cytological examination even in hospitals in which cytologists are not available. For such a specimen however, a relatively large amount of liquid is required which is a disadvantage when the specimen is to be sent by mail to the laboratory. In addition, since the specimen must be fixed to prevent the cells from being destroyed, which is made by adding a liquid fixative, the amount of liquid will be further increased.

In order to reduce the volume of the liquid it would be desirable to provide a concentrate of a urine specimen with a high percentage of body cells. However, a simple and reliable method and equipment for this purpose has hitherto not been presented.

Patients with urethra cancer have often had a urinary bladder inconvenience for a long time, such as half a year, before a correct diagnosis is made. At an early stage the diagnosis of urethra infection is usually made and the patient is treated therefore for a long time. When such treatment does not produce the desired result, the mucous membrane of the bladder is inspected by means of an instrument, so called cystoscope, in order to establish the possible presence of cancer. This examination is painful and must often be carried out under narcotics. In addition, cancer cells are often present in the urine before the tumour has become visible in the urinary bladder.

SUMMARY OF THE INVENTION

The object of the present invention is to eliminate the above mentioned drawbacks and to make it possible to discover especially cancer in the urinary bladder at an early stage and in a manner that is comfortable for the patient and simple and reliable for the medical staff. In order to fulfill this object a method of processing a body liquid specimen intended for diagnostical examination is proposed which according to the invention is characterized by bringing the specimen to settle for a predetermined time in a first chamber of a container, said container having a second separate chamber containing a certain amount of a fixative; separating and confining a portion of the specimen containing a predetermined amount of concentrate having a high concentration of settled body cells in a third chamber which is formed by partitioning off a portion of the first chamber; removing the remaining body liquid from the container; and interconnecting said second and third chambers in order to form a common, sealed chamber in which the concentrate is mixed with the fixative.

The invention also relates to a device for accomplishing the above method. The device according to the invention comprises a container of a tubular, flexible material and having a first chamber (settling chamber), a second separate chamber containing a certain amount of fixative, means for partitioning off a portion of said first chamber after the settling in order to form a third, separate chamber containing the settled concentrate, and means arranged to subsequently interconnect said second and third chambers.

BRIEF DESCRIPTION OF THE DRAWING

The invention will be described in more detail below with reference to the accompanying drawing, in which FIGS. 1 and 2 illustrate a front elevational view and a side elevational view, respectively, of a first embodiment of the device according to the invention in the position occupied during settling.

FIGS. 3 and 4 illustrate corresponding views of the device containing the completed specimen.

FIG. 5 is a front elevational view of a clip for sealing the device.

DESCRIPTION OF THE PREFERRED EMBODIMENTS

Figure 6:
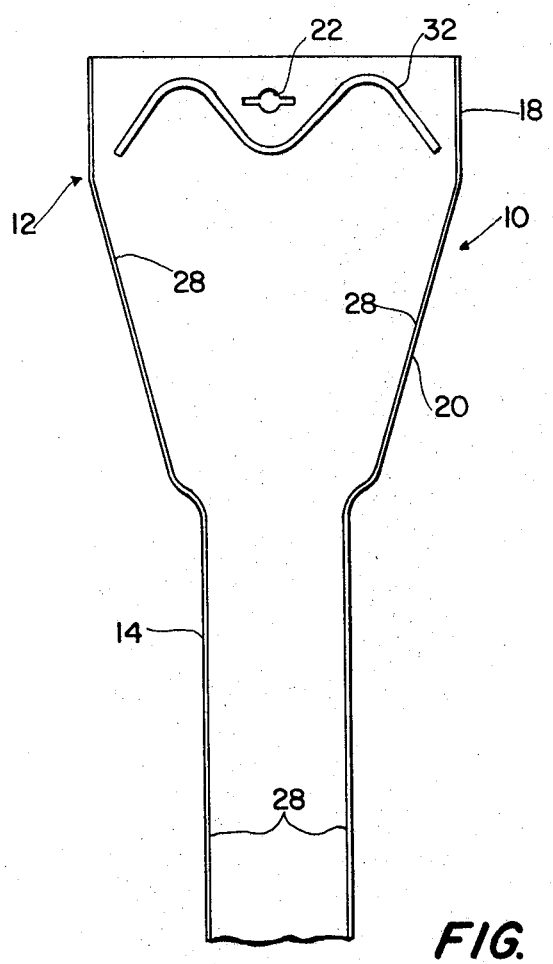
FIG. 6 is a front elevational view of a second embodiment of the device according to the present invention and FIG. 7 is a perspective view of the top portion of the device depicted in FIG. 6.

The device illustrated in FIGS. 1 and 2 comprises a tubular container 1 which is preferably made of a flexible plastic material. The container is provided at its upper end with a collapsable hopper 2, and a label 3 for the identification of the specimen is attached to the lower end thereof. The bottom portion 1a of the container 1 contains a fixative and is separated by means of a releasable clip 4. The fixative may comprise alcohol and acetic acid and have a volume of about 5 ml.

When using the device, about 200 ml urine is filled into the upper portion 1b of the container and the device is subsequently hung up in a vertical position on a hook or the like (not shown). For this purpose the hopper 2 is provided with an opening 2a. The position of the liquid surface in the container is indicated at 5. The specimen is then left to settle, the body cells sinking to the bottom of the upper portion 1b of the container. Assuming that the container has a diameter of 25 mm and a length of 400 mm, a settling time of 15–30 minutes is sufficient for obtaining a suitable cell concentrate.

When the settling time is over, an additional clip 4 indicated in dashed lines in FIG. 1 is applied to a position above the first mentioned clip. The position of the second clip is indicated by a marking 6 on the container 1. Thereby a urine specimen of a volume of about 5 ml and having a concentrated content of body cells is separated and enclosed between the two clips 4. The portion of the urine specimen which is above the upper clip is poured out of the container, the major part of the upper portion thereof, which is now empty, being subsequently cut off and removed.

The lower clip 4 is then removed from the container 1, the concentrated urine specimen being connected to the fixative in the lower container portion 1a and mixed therewith. The cells present in the urine specimen are thereby fixed and their metabolism ceases. The urine specimen processed in this way is durable for a practically unlimited time.

If desired, the removed clip can be used for sealing the free, cut off end of the container 1 as an extra measure of safety against leakage, as is shown in FIGS. 3 and 4.

The clip shown in FIG. 5 is preferably made of plastic material and comprises two legs 7, 8 which are hingedly interconnected at one end and are provided with an interlocking mechanism at the other end. One leg 7 is provided with an elastic rubber element 9 securing effective sealing when in closed position.

The label 3 attached to the container 1 is provided with the name and other information about the patient or other necessary information enabling a certain identification of the specimen.

Figure 7:
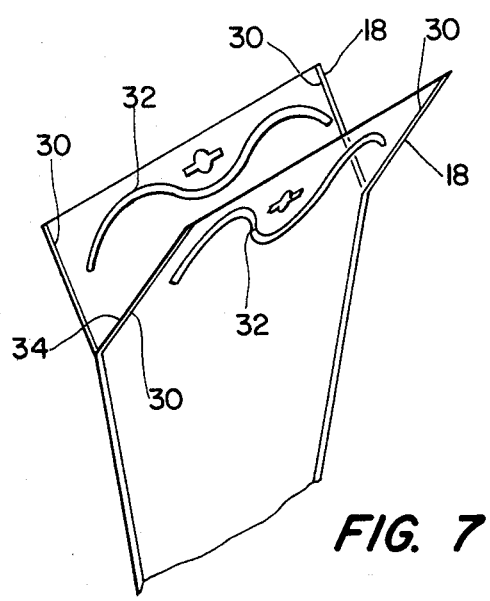

A second embodiment of a device according to the present invention is illustrated in FIGS. 6 through 12. With particular reference to FIGS. 6 and 7, the device comprises a container 10 having an open, funnel top portion 12 and an integral, elongated body portion 14 with a closed end portion 16. Top portion 12, as seen in an elevational view, has a reinforced upper rectangular part or flap 18 and a lower, truncated conical hopper 20. An elongated orifice 22 in top rectangular part 18 is provided to permit container 10 to be vertically hung from a post (not shown).

Container 10 is comprised of two sheets 24 and 26 of fluid-tight plastic sheet material (see also FIG. 8) that are heat sealed together at a fusion line 28 along the peripheries thereof. A presently preferred method of producing container 10 having a reinforced top portion 12 is to fold longitudinally in half a single pattern having longitudinal symmetry so as to produce a container shape similar to that depicted in FIG. 1. An inward tuck is then made at the folded end so as to produce the two rectangular parts or flaps 18, shown in FIG. 7. Sheets 24 and 26 are heat sealed together along fusion line 28 and along a fusion line 30 in each flap 18. A thick, undulating heat sealed line 32 is then made from the same side in each flap 18 in corresponding, mating positions so as to provide transverse rigidity to each flap and some sealing protection to container 10 when it is being hung from a post. Finally, the fold where the flaps 18 are connected is cut along a line 34 to provide an opening into container 10.

Figure 8:
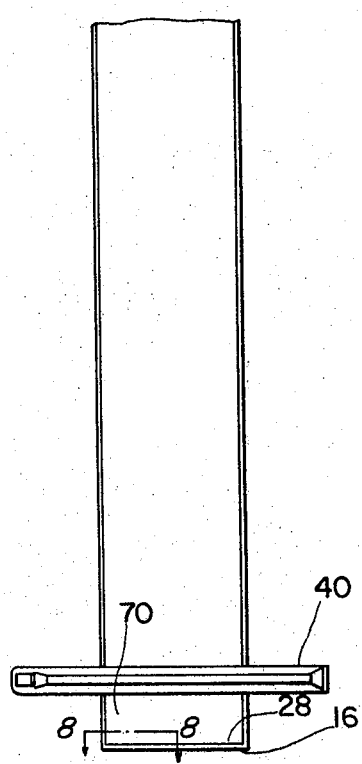
FIG. 8 is a greatly enlarged, cross-sectional view taken along line 8—8 of FIG. 6 illustrating the two plies of the container.

As shown in FIG. 8, each of plastic sheets 24 and 26 is two-ply, comprised of an outer ply 36 and an inner ply 38. Outer ply 36 is made of a conventional, diffusion-tight plastic and forms the fluid-tight boundry for container 10. Inner ply 38 is made of a conventional gluing-type plastic so that sheets 24 and 26 can be heat sealed together.

A modified clip 40 for use with container 10 is depicted in FIGS. 10 through 13. Clip 40 is preferably made of plastic material and comprises a first, male leg 42, a second, female leg 44 and a plastic material hinge 46 connecting legs 42 and 44 at one end. Located at the other end of clip 40 is a snap-fit interlocking mechanism comprised of a stud 48 resiliently connected to the end of first leg 42 and an annular catch 50 connected to the end of second leg 44. At the distal end of stud 48 there is a detent member 52 having an inclined forward surface 54. Catch 50 has an annular collar 56 and a central orifice 58 for receiving stud 48. Projecting from the inner face of male leg 42 is a rib 60 having parallel side walls 61. A mating slot 62 for rib 60 having parallel side walls 63 is provided in the inner face of female leg 44. Slot 62 is wider than rib 60 by a distance slightly less than twice the thickness of elongated body portion 14. At either end of rib 60 there is a raised section 64, the distance between the raised section 64 being slightly less than the width of elongated body portion 14.

Figure 9:
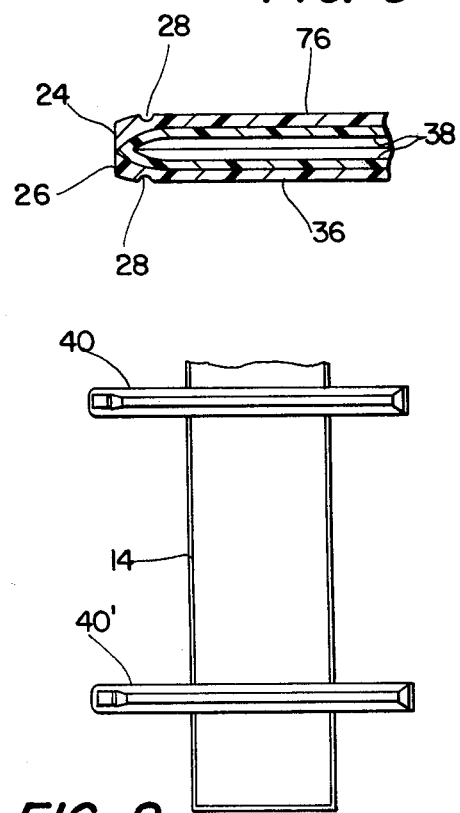
FIG. 9 is a front elevational view of the device depicted in FIG. 6 illustrating the completed specimen.
Figure 10:
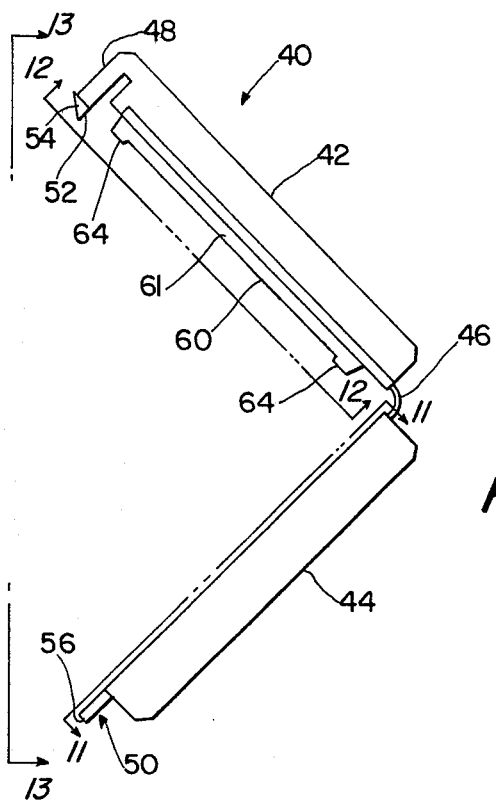
FIG. 10 is a front elevational view of a modified clip for sealing the container.
Figure 11:
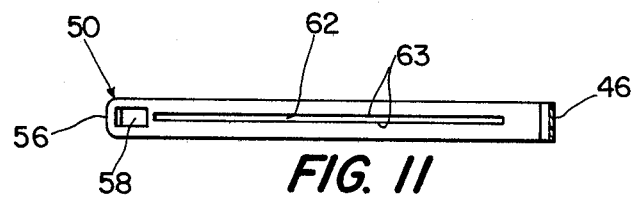
FIGS. 11 and 12 are plan views thereof taken along lines 11—11 and 12—12 of FIG. 10, respectively.
Figure 12:
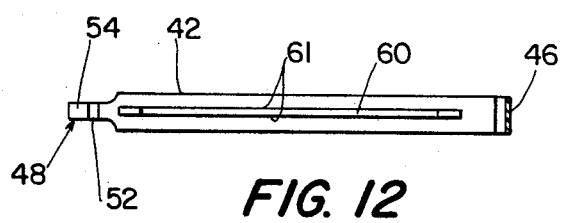
Figure 13:
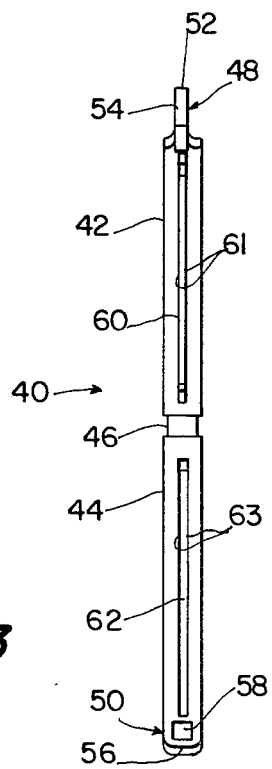
FIG. 13 is an end view taken along line 13—13 of FIG. 10.

In use, the second embodiment of the present invention is used much like the first embodiment described above. With the second embodiment, the 5 ml volume of fixative is located in the bottom portion 70 which is closed off from the rest of elongated body portion 14 by a clip 40. The filling of the upper portion of elongated body portion 14 with approximately 200 ml of urine is facilitated by funnel top portion 12 which is easily held open by reinforced flaps 18. After the device is hung up by use of orifice 22, the sample is left to settle. After the appropriate time, a second clip 40' is applied above clip 40, and clip 40 is removed. As shown in FIG. 9, the fixative and sample mix in the portion of elongated body portion 14 located below clip 40'. After the urine specimen remaining above clip 40' is disposed of, most of the upper end of elongated body portion 14 is removed. As an added precaution against leakage, clip 40 is also applied above clip 40' to the remaining section of elongated body portion 14.

In applying clips 40 and 40' to elongated body portion 14, it should be noted that elongated body portion 14 is positively located between raised sections 64 of rib 60 so that elongated body portion 14 is positively clamped between the sides 61 of rib 60 and the sides 63 of slot 62 as stud 48 passes through orifice 58 of catch 50 and is locked in place. In addition, as elongated body portion 14 is forced into slot 62 by rib 60 as clip 40 is closed, the area of elongated body portion 14 on either side of rib 60 is sealed by adjacent sides 61 and 63, providing two liquid tight seals at the clip.

Container 10 may receive a label applied along its length. Preferably, this label is applied to plastic containers 10 by printing on a suitably prepared (i.e., by electron bombardment) portion of container 10. In this manner, the relevant patient data is applied by the physician directly on the printed label area.

The specimen obtained by accomplishing the above described invention has all the desired advantages, such as high concentration of body cells, good durability, small volume and low weight. Therefore, the specimen is well adapted for being forwarded by mail to a cytological laboratory for examination. To this end the specimen is disposed in a suitable liquid-proof envelope.

Further, it should be easily realized that the above described method and apparatus can be performed without difficulties by the ordinary medical staff without the need for special education or skill and also without any expensive and complicated equipment.

I claim:

1. A method of processing a urine specimen for diagnostic examination, comprising the steps of:
   introducing a fixative into the lower, closed end of an elongated tube formed of flexible material;
   closing the tube with a first removable clip just above the portion containing the fixative;
   introducing the urine specimen into the tube through a collapsible hopper which forms an open upper end of the tube and which funnels the urine down into said tube just above said removable clip;
   permitting the urine specimen to separate, by settlement, to form a concentrate having a higher concentration of settled body cells than the rest of the urine specimen, and such that said concentrate is located adjacent the said removable clip;
   applying a further removable clip across the first chamber of said tube to separate some or all of said concentrate from the remainder of the urine specimen therein;
   removing said first removable clip to place said concentrate and said fixative into communication with each other to mix said concentrate with said fixative; and
   removing the remainder of the urine specimen from said tube.

2. A method of processing a urine specimen according to claim 1 further including the step of applying a clip to the tube above said further clip after removal of the remainder of the urine specimen from said tube to thereby further secure the sealing of said tube for transportation and handling.

* * * * *